US00PP18042P2

(12) United States Plant Patent
Hanes

(10) Patent No.: US PP18,042 P2
(45) Date of Patent: Sep. 18, 2007

(54) ***PELARGONIUM* PLANT NAMED 'FREE RURED'**

(50) Latin Name: *Pelargonium peltatum*
Varietal Denomination: Free Rured

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/370,268

(22) Filed: Mar. 7, 2006

(51) Int. Cl.
*A01H 5/00* (2006.01)

(52) U.S. Cl. ..... Plt./332

(58) Field of Classification Search ..... Plt./332
See application file for complete search history.

*Primary Examiner*—Anne Marie Grunberg
*Assistant Examiner*—Georgia Helmer
(74) *Attorney, Agent, or Firm*—Jondle & Associates, P.C.

(57) ABSTRACT

A new *pelargonium* plant particularly distinguished by dark-red, double flowers, floriferous with small to medium-sized semi-spherically shaped inflorescences, grass-green foliage, small leaves with weak zonation, medium vigor, medium sized, tight, compact, round and well-branched plant habit, initially spreading, later decumbent to somewhat trailing plant habit with an early flowering response, is disclosed.

1 Drawing Sheet

Genus and species: *Pelargonium peltatum* L'Héritier.
Variety denomination: 'Free Rured'.

BACKGROUND OF THE NEW PLANT

The present invention comprises a new and distinct cultivar of *pelargonium,* botanically known as a *Pelargonium peltatum* L'Héritier, and hereinafter referred to by the cultivar name 'Free Rured'. The new cultivar was propagated from a seedling resulting from the cross of the female parent '8652-2', a dark-red-flowered proprietary *pelargonium* plant (unpatented) and the male parent '8653-8' (unpatented) a proprietary *pelargonium* plant having burgundy-red flowers.

The new cultivar was created in 2002 in Gilroy, Calif. and has been asexually reproduced repeatedly by vegetative cuttings and tissue culture in Gilroy, Calif. and Hillscheid, Germany over a three-year period. The present invention has been found to retain its distinctive characteristics through successive asexual propagations.

Plant Breeder's Rights for this cultivar were applied for in Canada on Mar. 29, 2005 and with the European Union on Sep. 20, 2005.

SUMMARY OF THE INVENTION

The following are the most outstanding and distinguishing characteristics of this new cultivar when grown under normal horticultural practices in Gilroy, Calif. and Hillscheid, Germany.

1. Dark-red, double flowers;
2. Floriferous with small to medium-sized, semi-spherically-shaped inflorescences;
3. Green-green foliage, relatively small leaves with weak zonation;
4. Medium vigor, medium, tight and compact plant habit;
5. Initially spreading, later decumbent to somewhat trailing, rounded and well-branched plant habit; and
6. An early flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of an above view of three 25-week-old plants grown in a greenhouse in mid-Summer in Hillscheid, Germany.

DESCRIPTION OF THE NEW CULTIVAR

The following detailed description sets forth the distinctive characteristics of 'Free Rured'. The data which define these characteristics were collected from asexual reproductions carried out in Hillscheid, Germany. The plant history was taken on 13-week old plants which were planted as rooted cuttings in 12-cm pots in late May 2005 and grown in a greenhouse. The plants were pinched once. Color readings were taken under natural light in mid-May from flowers grown in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Genaniaceae.
- *Botanical.*—*Pelargonium peltatum* L'Héritier.
- *Common name.*—Ivy geranium.

Parentage:
- *Female parent.*—'8652-2' a proprietary dark-red flowered *pelargonium* plant (unpatented).
- *Male parent.*—'8653-8', a proprietary *pelargonium* plant having burgundy-red flowers (unpatented).

Growth:
- *Form.*—Shrub, self-branching, rounded shape.
- *Branching habit.*—11.0 branches per plant.
- *Height* (*measured from the top of the soil, excluding the inflorescence*).—19.7 cm.

*Width* (*horizontal plant spread*).—37 cm.
*Plant size in late summer* (*plant radius, measured from the plant base to the tips*).—30 week-old plant developed branches of 55 cm in length.
*Time to produce a finished flowering plant.*—About 11 to 12 weeks for a 12-cm to 14-cm pot in the Spring.
*Outdoor plant performance.*—Plants continuously flower; a count in early September of 30-week old plants in Hillscheid, Germany produced about 20 inflorescences per plant.
*Time to initiate and develop roots.*—About 24 days at 20° C.
*Root description.*—Fibrous.

Leaves:
*Arrangement.*—Opposite on flowering branches.
*Immature leaf color.*—Upper surface: RHS 143A (grass-green). Lower surface: Between RHS 143B.
*Mature leaf color.*—Upper surface: RHS 143A (grass-green). Lower surface: RHS 143B.
*Size.*—Length: 4.7 cm. Width: 8.2 cm.
*Apex.*—Rounded.
*Base.*—Cordate or sub-cordate.
*Shape.*—Ivy-shaped with most often only weak lobes, the lowest lobes form an obtuse angle.
*Margin.*—Entire.
*Texture.*—Upper surface: Smooth, leathery and glossy. Lower surface: Protruding veins in palmate arrangement.
*Zonation color.*—RHS 147A, absent to weak.
*Zonation diameter.*—1.6 cm, the zone is a small ring close to the leaf base.
*Venation type.*—Palmate.
*Venation color.*—RHS 145A (pale-green).
*Petioles.*—Color: RHS 143C (light-green). Length: About 5 cm to 8 cm. Diameter: 0.2 cm. Texture: Covered with very short, fine pubescence.

Stems:
*Number of branches.*—11.
*Stem color.*—RHS 143B (light-green).
*Length.*—27.7 cm.
*Diameter* (*at mid-point*).—About 0.4 cm.
*Internode length.*—1.5 cm to 3.0 cm.
*Texture.*—Smooth, glabrous.

Inflorescence bud:
*Shape.*—Broadly elliptical.
*Size.*—Length: 1.7 cm. Width: 1.2 cm.
*Color of sepals* (*just before petals unfold*).—RHS 137D (green).
*Color of petals* (*just before petals unfold*).—RHS 61B (purple-red).

Inflorescence:
*Blooming habit.*—Continuous from Spring to Fall.
*Inflorescence type.*—An umbel composed of 9 to 15 flowers.
*Umbel.*—Shape: Semi-spherical or nearly semi-spherical, tight. Diameter: 8.8 cm. Height (depth): 4.0 cm to 4.5 cm.
*Lastingness of umbel on the plant.*—About 15 to 17 days.
*Flowering response.*—Average of 5 open inflorescences 13 weeks after planting rooted cuttings.
*Lastingness of individual flowers on plant.*—6 to 9 days at 18° C.
*Fragrance.*—None.
*Peduncle.*—Color: RHS 143C (light-green). Length: 11.3 cm. Diameter: 0.3 cm. Texture: Smooth with sparse, short hairs.
*Pedicel.*—Color: Mainly RHS 143C (light-green), RHS 146A (olive-green) near the flower base. Length: 2.6 cm. Diameter: 0.1 cm. Texture: Short, fine pubescence.

Corolla:
*Shape of corolla.*—Round outline with both the upper petals and lower petals roughly of the same size.
*Form.*—Double.
*Diameter.*—5.1 cm.
*Number of petals.*—About 20 to 30.
*Petaloids.*—Shape: Variable, narrower and shorter than the petals, threadlike, with tube-shaped base or like a small petal. Number: 2 to 5. Color: RHS 155A (white) at the base, upper end may correspond to petal color or be a slightly less deep-red hue; RHS 46B to RHS 46C.

Petals:
*Shape.*—Obovate.
*Apex.*—Rounded.
*Base.*—Acute.
*Margin.*—Entire or slightly crenated at the tips.
*Texture.*—Smooth, slightly glossy.
*Upper petals.*—Length: 2.8 cm to 3.0 cm. Width: 1.7 cm to 1.9 cm. Color: Upper surface: Mainly RHS 46A (dark-red), RHS 46B near the bases. Lower surface: RHS 53C (dull red-purple). Markings: Two nearly black veins, RHS 187A.
*Lower petals.*—Length: 2.6 cm to 2.8 cm. Width: 1.5 cm to 1.6 cm. Color: Upper surface: From RHS 46A to RHS 46B. Lower surface: RHS 53C. Markings: Absent.

Sepals:
*Number.*—5 to 6.
*Color.*—RHS 143C (light-green) for both surfaces, no anthocyanin.
*Length.*—1.1 cm.
*Width.*—Largest upper sepal: 0.4 cm. Other sepals: 0.2 cm.
*Shape.*—Ligulate to ensiform.
*Apex.*—Acute.
*Base.*—Fused.
*Margin.*—Entire.
*Texture.*—Relatively long, fine hairs.

Reproductive organs:
*Androecium.*—Number of anthers: 0 to 3. Filament length: 1.0 cm. Filament color: RHS 155A (whitish). Filament diameter: 0.1 cm. Pollen color: RHS 23A (yellow-orange). Pollen amount: Little.
*Gynoecium: Pistil: Number:* 1. Length: 0.10 cm to 0.11 cm. Diameter: 0.1 cm. Stigma color: RHS 53A (deep-red). Stigma shape: 5- to 6 -lobed, at right angles to the style. Style color: RHS 155A (whitish). Style length: 0.3 cm to 0.4 cm. Style shape: Filiform (filament-like) with the lobes of the stigma at right angles.

Fruit and seed set: No seed set observed.

Disease and insect resistance: No particular resistance or susceptibility has been observed.

COMPARISON WITH PARENTAL AND COMMERCIAL CULTIVARS

'Free Rured' differs from the female parent '8652-2' (unpatented) by having deeper green leaves, more evenly shaped flowers and an earlier flowering response than '8652-2'.

'Free Rured' differs from the male parent '8653-8' (unpatented) by having dark-red flowers while '8653-8' has burgundy-red flowers. In addition, 'Free Rured' has deeper green foliage and an earlier flowering response than '8653-8'.

'Free Rured' differs from the commercial variety 'Fisruby' (U.S. Plant Patent Applied for) by having flowers with more petals and a smaller inflorescence with shorter peduncles than 'Fisruby'. In addition, 'Free Rured' has foliage with weaker to no zonation when compared to 'Fisruby'.

'Free Rured' differs from the commercial variety 'Free Dark Red' (U.S. Plant Pat. No. 12,446) by having darker-red flowers than 'Free Dark Red'. In addition, 'Free Rured' has shorter peduncles, weaker to no zonation on the leaves and a tighter, more compact and shorter plant habit than 'Free Dark Red'.

I claim:

1. A new and distinct cultivar of *pelargonium* plant as shown and described herein.

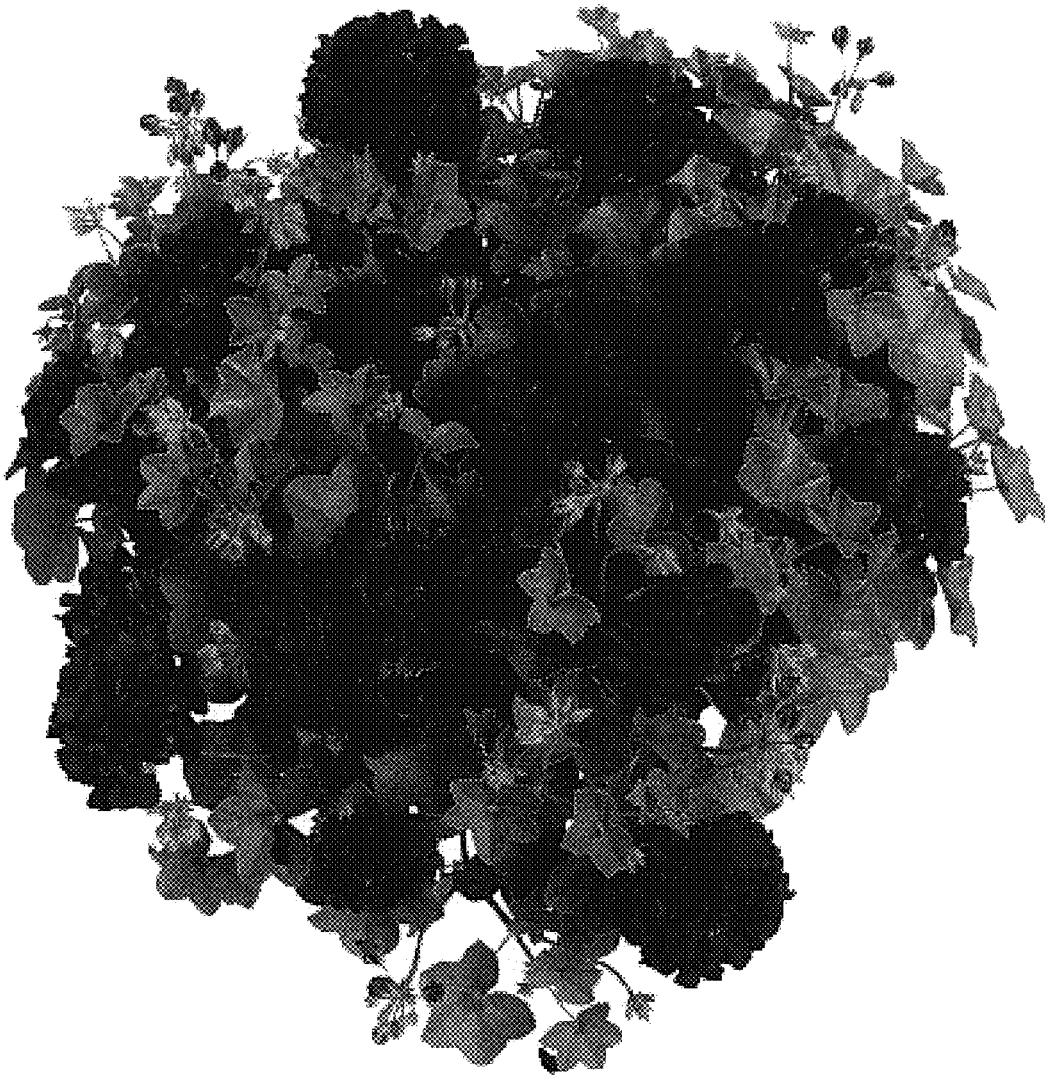

* * * * *